United States Patent
Tabirian et al.

(10) Patent No.: US 10,274,805 B2
(45) Date of Patent: Apr. 30, 2019

(54) POLARIZATION-INDEPENDENT SWITCHABLE LENS SYSTEM

(71) Applicant: Beam Engineering for Advanced Materials Co., Orlando, FL (US)

(72) Inventors: Nelson V. Tabirian, Winter Park, FL (US); David E. Roberts, Apopka, FL (US)

(73) Assignee: Beam Engineering for Advanced Measurements Co., Orlando, FL (US)

( * ) Notice: Subject to any disclaimer, the term of this patent is extended or adjusted under 35 U.S.C. 154(b) by 0 days.

(21) Appl. No.: 15/621,553

(22) Filed: Jun. 13, 2017

(65) Prior Publication Data

US 2018/0356704 A1     Dec. 13, 2018

(51) Int. Cl.
   *G02C 7/08*       (2006.01)
   *G02F 1/29*       (2006.01)
   (Continued)

(52) U.S. Cl.
   CPC .............. *G02F 1/29* (2013.01); *A61F 2/1627* (2013.01); *A61F 2/1635* (2013.01); *G02C 7/041* (2013.01);
   (Continued)

(58) Field of Classification Search
   CPC . G02C 7/04; G02C 7/08; G02C 7/081; G02C 7/083; G02C 7/086; G02C 7/41; G02F 1/29; A61F 2/1627; A61F 2/1635
   (Continued)

(56) References Cited

U.S. PATENT DOCUMENTS

| 2,435,616 A | 2/1948 | Vittum |
| 3,721,486 A | 3/1973 | Bramley |

(Continued)

FOREIGN PATENT DOCUMENTS

| EP | 1970734 | 9/2008 |
| EP | 2088456 | 12/2009 |

(Continued)

OTHER PUBLICATIONS

Nersisyan, S., et al., "Optical Axis Gratings in Liquid Crystals and Their Use for Polarization Insensitive Optical Switching," Journal of Nonlinear Optical Physics & Materials, vol. 18, 2009, 47 pages.

(Continued)

*Primary Examiner* — Stephone B Allen
*Assistant Examiner* — Travis S Fissel
(74) *Attorney, Agent, or Firm* — Brian S. Steinberger; Law Offices of Brian S. Steinberger, P.A.

(57) ABSTRACT

Energized lens systems and methods of fabricating an energized lens system which can be switched from one polarization-independent focal length to another polarization-independent focal length. The energized lens system can include a 90 degree twisted nematic liquid crystal layer with curved boundaries, and with transparent conductive electrodes which allow the application of an electric field to switch the focal length of the twisted nematic liquid crystal layer. The focal length of the energized lens system can be independent of the polarization of light in both of its two states, and only one liquid crystal layer of the energized lens system needs to be switched in order for the focal length of the energized lens system to be switched.

13 Claims, 7 Drawing Sheets

(51) Int. Cl.
*G02C 7/04* (2006.01)
*A61F 2/16* (2006.01)

(52) U.S. Cl.
CPC .......... *G02C 7/083* (2013.01); *G02F 2202/40* (2013.01); *G02F 2203/06* (2013.01)

(58) Field of Classification Search
USPC ............ 351/159.01, 159.03, 159.05, 159.39, 351/159.4, 159.55, 159.73, 159.75, 351/159.76, 178
See application file for complete search history.

(56) References Cited

U.S. PATENT DOCUMENTS

| | | | |
|---|---|---|---|
| 3,897,136 A | 7/1975 | Bryngdahl | |
| 4,160,598 A | 7/1979 | Firester et al. | |
| 4,301,023 A | 11/1981 | Schuberth | |
| 4,698,816 A | 10/1987 | Chun | |
| 4,956,141 A | 9/1990 | Allen | |
| 4,983,332 A | 1/1991 | Hahn | |
| 5,032,009 A | 7/1991 | Gibbons | |
| 5,042,950 A | 8/1991 | Salmon, Jr. | |
| 5,047,847 A | 9/1991 | Toda | |
| 5,100,231 A | 3/1992 | Sasnett et al. | |
| 5,142,411 A | 8/1992 | Fiala | |
| 5,150,234 A | 9/1992 | Takahashi | |
| 5,218,610 A | 6/1993 | Dixon | |
| 5,321,539 A | 6/1994 | Hirabayashi | |
| 5,325,218 A | 6/1994 | Willett | |
| 5,446,596 A | 8/1995 | Mostrorocco | |
| 5,621,525 A | 4/1997 | Vogeler et al. | |
| 5,712,721 A * | 1/1998 | Large | A61F 2/1613 351/158 |
| 5,895,422 A | 4/1999 | Hauber | |
| 5,903,330 A | 5/1999 | Funschilling | |
| 5,989,758 A | 11/1999 | Komatsu | |
| 6,091,471 A * | 7/2000 | Kim | G02F 1/133753 349/124 |
| 6,107,617 A | 8/2000 | Love et al. | |
| 6,139,147 A | 10/2000 | Zhang | |
| 6,170,952 B1 | 1/2001 | La Haye et al. | |
| 6,191,880 B1 | 2/2001 | Schuster | |
| 6,219,185 B1 | 4/2001 | Hyde | |
| 6,320,663 B1 | 11/2001 | Ershov | |
| 6,373,549 B1 | 4/2002 | Tombling et al. | |
| 6,452,145 B1 | 9/2002 | Graves et al. | |
| 6,551,531 B1 | 4/2003 | Ford | |
| 6,678,042 B2 | 1/2004 | Tabirian et al. | |
| 6,728,049 B1 | 4/2004 | Tabirian et al. | |
| 6,792,028 B2 | 9/2004 | Cook | |
| 6,911,637 B1 | 6/2005 | Vorontsov et al. | |
| 7,048,619 B2 | 5/2006 | Park | |
| 7,094,304 B2 | 8/2006 | Nystrom | |
| 7,095,772 B1 | 8/2006 | Delfyett et al. | |
| 7,196,758 B2 | 3/2007 | Crawford | |
| 7,319,566 B2 | 1/2008 | Prince | |
| 7,324,286 B1 | 1/2008 | Glebov | |
| 7,450,213 B2 | 11/2008 | Kim et al. | |
| 7,482,188 B2 | 1/2009 | Moon | |
| 7,764,426 B2 | 7/2010 | Lipson | |
| 8,045,130 B2 | 10/2011 | Son | |
| 8,077,388 B2 | 12/2011 | Gerton | |
| 8,264,623 B2 | 9/2012 | Marrucci | |
| 8,520,170 B2 | 8/2013 | Escuti | |
| 8,582,094 B1 | 11/2013 | Shortt | |
| 8,643,822 B2 | 2/2014 | Tan et al. | |
| 8,937,701 B2 | 1/2015 | Rossini | |
| 8,982,313 B2 | 3/2015 | Escuti et al. | |
| 9,541,772 B2 | 1/2017 | De Sio | |
| 9,557,456 B2 | 1/2017 | Tabirian et al. | |
| 9,592,116 B2 | 3/2017 | De Sio | |
| 9,617,205 B2 | 4/2017 | Tabirian et al. | |
| 9,658,512 B2 | 5/2017 | Tabirian et al. | |
| 9,715,048 B2 | 7/2017 | Tabirian et al. | |
| 9,753,193 B2 | 9/2017 | Tabirian et al. | |
| 9,976,911 B1 | 5/2018 | Tabirian et al. | |
| 9,983,479 B2 | 5/2018 | Tabirian et al. | |
| 10,031,424 B2 | 7/2018 | Tabirian et al. | |
| 10,036,886 B2 | 7/2018 | Tabirian et al. | |
| 10,075,625 B2 | 9/2018 | Tabirian et al. | |
| 10,107,945 B2 | 10/2018 | Tabirian et al. | |
| 10,114,239 B2 | 10/2018 | Tabirian et al. | |
| 10,120,112 B2 | 11/2018 | Tabirian et al. | |
| 10,185,182 B2 | 1/2019 | Tabirian | |
| 10,191,191 B2 | 1/2019 | Tabirian et al. | |
| 10,197,715 B1 | 2/2019 | Tabirian et al. | |
| 2001/0002895 A1 | 6/2001 | Kawano | |
| 2001/0018612 A1 | 8/2001 | Carson et al. | |
| 2001/0030720 A1 | 10/2001 | Ichihashi | |
| 2002/0027624 A1 | 3/2002 | Seiberle | |
| 2002/0097361 A1 | 7/2002 | Ham | |
| 2002/0167639 A1 | 11/2002 | Coates | |
| 2003/0021526 A1 | 1/2003 | Bouevitch | |
| 2003/0072896 A1 | 4/2003 | Kwok | |
| 2003/0137620 A1 * | 7/2003 | Wang | G02B 5/3016 349/95 |
| 2003/0152712 A1 | 8/2003 | Motomura | |
| 2003/0206288 A1 | 11/2003 | Tabirian et al. | |
| 2003/0214700 A1 | 11/2003 | Sidorin | |
| 2003/0218801 A1 | 11/2003 | Korniski et al. | |
| 2004/0051846 A1 | 3/2004 | Blum et al. | |
| 2004/0081392 A1 | 4/2004 | Li | |
| 2004/0105059 A1 | 6/2004 | Ofiyama | |
| 2004/0165126 A1 | 8/2004 | Ooi et al. | |
| 2005/0030457 A1 | 2/2005 | Kuan et al. | |
| 2005/0110942 A1 | 5/2005 | Ide | |
| 2005/0219696 A1 | 10/2005 | Albert et al. | |
| 2005/0271325 A1 | 12/2005 | Anderson et al. | |
| 2005/0276537 A1 | 12/2005 | Frisken | |
| 2005/0280717 A1 | 12/2005 | Chen | |
| 2006/0008649 A1 | 1/2006 | Shinichiro | |
| 2006/0055883 A1 | 3/2006 | Morris et al. | |
| 2006/0109532 A1 | 5/2006 | Savas | |
| 2006/0221449 A1 | 10/2006 | Glebov et al. | |
| 2006/0222783 A1 | 10/2006 | Hayashi | |
| 2007/0032866 A1 | 2/2007 | Portney | |
| 2007/0040469 A1 | 2/2007 | Yacoubian | |
| 2007/0115551 A1 | 5/2007 | Spilman | |
| 2007/0122573 A1 | 5/2007 | Yasuike | |
| 2007/0132930 A1 | 6/2007 | Ryu et al. | |
| 2007/0247586 A1 | 10/2007 | Tabirian | |
| 2007/0258677 A1 | 11/2007 | Chigrinov | |
| 2008/0226844 A1 | 9/2008 | Shemo | |
| 2008/0278675 A1 | 11/2008 | Escuti | |
| 2009/0002588 A1 | 1/2009 | Lee et al. | |
| 2009/0052838 A1 * | 2/2009 | McDowall | G02F 1/0136 385/18 |
| 2009/0073331 A1 | 3/2009 | Shi | |
| 2009/0122402 A1 | 5/2009 | Shemo | |
| 2009/0141216 A1 | 6/2009 | Marrucci | |
| 2009/0201572 A1 | 8/2009 | Yonak | |
| 2009/0256977 A1 | 10/2009 | Haddock | |
| 2009/0257106 A1 | 10/2009 | Tan | |
| 2009/0264707 A1 | 10/2009 | Hendricks | |
| 2010/0003605 A1 | 1/2010 | Gil | |
| 2010/0066929 A1 | 3/2010 | Shemo | |
| 2010/0245954 A1 | 9/2010 | Ahling | |
| 2011/0069377 A1 | 3/2011 | Wu et al. | |
| 2011/0075073 A1 | 3/2011 | Oiwa | |
| 2011/0085117 A1 | 4/2011 | Moon et al. | |
| 2011/0097557 A1 | 4/2011 | May | |
| 2011/0109874 A1 | 5/2011 | Piers et al. | |
| 2011/0135850 A1 | 6/2011 | Saha et al. | |
| 2011/0188120 A1 | 8/2011 | Tabirian et al. | |
| 2011/0234944 A1 | 9/2011 | Powers | |
| 2011/0262844 A1 | 10/2011 | Tabirian | |
| 2012/0075168 A1 | 3/2012 | Osterhout et al. | |
| 2012/0140167 A1 | 6/2012 | Blum | |
| 2012/0162433 A1 | 6/2012 | Fuentes Gonzalez | |
| 2012/0188467 A1 | 7/2012 | Escuti | |
| 2013/0057814 A1 | 3/2013 | Prushinskiy et al. | |
| 2013/0202246 A1 | 8/2013 | Meade | |
| 2014/0055740 A1 | 2/2014 | Spaulding | |

(56) References Cited

U.S. PATENT DOCUMENTS

| | | | |
|---|---|---|---|
| 2014/0211145 | A1 | 7/2014 | Tabirian |
| 2014/0252666 | A1 | 9/2014 | Tabirian |
| 2015/0049487 | A1 | 2/2015 | Connor |
| 2015/0081016 | A1 | 3/2015 | De Sio et al. |
| 2015/0276997 | A1 | 10/2015 | Tabirian et al. |
| 2016/0004100 | A1 | 1/2016 | Pugh |
| 2016/0011564 | A1 | 1/2016 | Tanabe et al. |
| 2016/0023993 | A1 | 1/2016 | Tabirian |
| 2016/0047955 | A1 | 2/2016 | Tabirian et al. |
| 2016/0047956 | A1 | 2/2016 | Tabirian et al. |
| 2016/0209560 | A1 | 7/2016 | Tabirian et al. |
| 2016/0231592 | A9 | 8/2016 | Beaton et al. |
| 2016/0266407 | A1 | 9/2016 | De Sio |
| 2016/0270909 | A1 | 9/2016 | De Sio |
| 2016/0363484 | A1 | 12/2016 | Barak et al. |
| 2016/0363783 | A1* | 12/2016 | Blum ............... G02C 7/049 |
| 2016/0363784 | A1 | 12/2016 | Beaton |
| 2017/0010397 | A1 | 1/2017 | Tabirian et al. |

FOREIGN PATENT DOCUMENTS

| | | |
|---|---|---|
| GB | 2209751 | 5/1989 |
| JP | 2001142033 | 5/2001 |
| JP | 2004226752 | 8/2004 |
| WO | 2007122573 | 11/2007 |
| WO | 2008130555 | 10/2008 |
| WO | 2008130559 | 10/2008 |

OTHER PUBLICATIONS

Tabirian, N., et al., "Thin Waveplate Lenses of Switcahable Focal Length—New Generation in Optics." Optics Express, vol. 23, Issue 20, 2015, 12 pages.

Kuo, C.-T., et al., "Electrically controllable Fresnel lens in 90 degree twisted nematic liquid crystals," Optics Express, vol. 23, Issue 20, 2015, 8 pages.

Syed, I, et al., "Novel switching mode in a vertically aligned liquid crystal contact lens," Optics Express, vol. 23, Issue 8, 2015, 6 pages.

Chen, H.-S., et al., "Electrically Tunable Ophthalmic Lenses for Myopia and Presbyopia Using Liquid Crystals," Molecular Crystals and Liquid Crystals, vol. 596, 2014, pp. 88-96, abstract, 3 pages.

Milton, H., et al., "Field-induced refractive index variation in the dark conglomerate phase for polarization-independent switchable liquid crystal lenses," Applied Optics, vol. 53, issue 31, 2014, pp. 7278-7284, abstract, 4 pages.

Lin, Y.-H., et al., "Electrically tunable-focusing and polarizer-free liquid crystal lenses for ophthalmic applications," Optics Express, vol. 21, Issue 8, 2013, 9 pages.

Lin, Y.-H., et al., "A polarization-independent liquid crystal phase modulation using polymer-network liquid crystals in 90 degree twist cell," Journal of Applied Physics, vol. 112, 2012, abstract, 8 pages.

Milton, et al., Field-Induced Refractive Index Variation in the Dark Conglomerate Phase for Polarization-Independent Switchable Liquid Crystal Lenses, Applied Optics, 2014, 6 pages.

Chen, et al., Electrically Tunable Opthalmic Lenses for Myopia and Presbyopia Using Liquid Crystals, Mol. Cryst. Liq. Cryst., Dec. 2014, pp. 88-96, vol. 596, 9 pages.

Anderson, G., et al., Broadband Antihole Photon Sieve Telescope, Applied Optics, vol. 16, No. 18., Jun. 2007, 3 pages.

Early, J. et al., Twenty Meter Space Telescope Based on Diffractive Fresnel Lens, SPIE, U.S. Department of Energy, Lawrence Livermore National Laboratory, Jun. 2003, 11 pages.

Martinez-Cuenca, et al., Reconfigurable Shack-Hartmann Sensor Without Moving Elements,Optical Society of America, vol. 35, No. 9, May 2010, 3 pages.

Serak, S., et al., High-efficiency 1.5 mm Thick Optical Axis Grating and its Use for Laser Beam Combining, Optical Society of America, vol. 32, no., Jan. 2007, 4 pages.

Ono et al., Effects of phase shift between two photoalignment substances on diffration properties in liquid crystalline grating cells, Appl. Opt. vol. 48, Jan. 2009, 7 pgs.

Naydenova et al., "Diffraction form polarization holographic gratings with surface relief in side chain azobenzene polyesters" J. Opt. Soc. Am. B, vol. 15, (1998), 14 pages.

Oh et al., Achromatic polarization gratings as highly efficent thin-film polarizing beamsplitters for broadband light Proc. SPIE vol. 6682, (2007), 4 pages.

Nersisyan, S., et al., Polarization insensitive imaging through polarization gratins, Optics Express, vol. 17, No. 3, Feb. 2, 2009, 14 pages.

OISE, Optics in the Southeast, Technical Conference and Tabletop Exhibit, Optical Society of America, Orlando, FL., Nov. 12-13, 2003, 9 pages.

Dierking, Polymer Network-Stabilized Liquid Crystals, Advanced Materials, vol. 12, No. 3, 2000, 15 pages.

Pepper, M. et al, Nonlinear Optical Phase Conjugation, IEEE, Sep. 1991, pp. 21-34, 14 pages.

Tabirian, N., Utility U.S. Appl. No. 14/194,808, filed Mar. 2, 2014, Office Action Summary dated Feb. 9, 2018, 10 pages.

Tabirian, N., Utility U.S. Appl. No. 14/324,126, filed Jul. 4, 2014, Office Action Summary dated Feb. 8, 2018, 13 pages.

De Sio, L., et al., "Digital Polarization Holography Advancing Geometrical Phase Optics," 2016, Optics Express, vol. 24, Issue 16, pp. 18297-18306, 10 pages.

Borek, G. and D. Brown, "High-performance diffractive optics for beam shaping," 1999, Proceeding of SPIE, vol. 3633, pp. 51-60, 10 pages.

Tabiryan, et al., The Promise of Diffractive Waveplates, OPN Optics and Photonics News, Mar. 2010, 6 pages.

Tabiryan, et al., Fabricating Vector Vortex Waveplates for Coronagraphy; Aerospace Conference, 2012, EEE; publicly available Apr. 19, 2012, 12 pages.

Tabirian, et al., PCT Application No. PCT/US15/26186 filed Apr. 16, 2015, Notification of Transmittal of the International Search Report and the Written Opinion of the International Searching Authority dated Jul. 14, 2015, 17 pages.

Nersisyan, et al., Study of azo dye surface command photoalignment material for photonics applications, Applied Optics, vol. 49, No. 10, Apr. 1, 2010, 8 pages.

Nersisyan, et al., Characterization of optically imprinted polarization gratings, Applied Optics, vol. 48, No. 21, Jul. 20, 2009, 6 pages.

Nersisyan, et al., Fabrication of Liquid Crystal Polymer Axial Waveplates for UV-IR Wavelengths, Optics Express, vol. 17, No. 14, Jul. 2009, 9 pages.

Tabirian, N., Utility U.S. Appl. No. 15/189,551, filed Jun. 22, 2016, Office Action Summary dated Feb. 27, 2018, 16 pages.

Nersisyan, et al., Polarization insensitive imaging through polarization gratings, Optics Express, vol. 17, No. 3, Feb. 2, 2009, 14 pages.

Sarkissian, et al., Longitudinally modulated nematic bandgap structure, Optical Society of America, vol. 23, No. 8, Aug. 2008, 6 pages.

Sarkissian, et al., Polarization-universal bandgap in periodically twisted nematics, Optics Letters, vol. 31, No. 11, Jun. 1, 2006, abstract, 4 pages.

Sarkissian, et al., Periodically Aligned Liquid Crystal: Potential Application for Projection Displays, Mol. Cryst. Liq. Cryst., vol. 451, 2006, 19 pages.

Sarkissian, et al., Potential application of Periodically Aligned Liquid Crystal cell for projection displays, JThE12, 2005, 3 pages.

Sarkissian, et al., Polarization-Controlled Switching Between Diffraction Orders in Transverse-Periodically Aligned Nematic Liquid Crystals, Optics Letters, Aug. 2006, abstract, 4 pages.

Schadt, et al., Photo-Induced Alignment and Patterning of Hybrid Liquid Crystalline Polymer Films on Single Substrates, Jpn. J. Appl. Phys., vol. 34, Part 2, No. 6B, Jun. 15, 1995, 4 pages.

Schadt , et al., Photo-Generation of Linearly Polymerized Liquid Crystal Aligning Layers Comprising Novel, Integrated Optically Patterned Retarders and Color Filters, Jpn. J. Appl. Phys., vol. 34, Part 1, No. 6A, Jun. 1995, 10 pages.

Schadt, et al., Optical patterning of multi-domain liquid-crystal displays with wide viewing angles, Nature, vol. 381, May 16, 1996, 4 pages.

(56) References Cited

OTHER PUBLICATIONS

Escuti, et al., A Polarization-Independent Liquid Crystal Saptial-Light-Modulator, Liquid Crystals X, Proc. of SPIE, vol. 6332, 2006, 9 pages.
Escuti, et al., Polarization-Independent LC Microdisplays Using Liquid Crystal Polarization Gratings: A Viable Solution (?), Dept of Electrical & Computer Engineering @ ILCC, Jul. 1, 2008, 30 pages.
Escuti, et al., Simplified Spectropolarimetry Using Reactive Mesogen Polarization Gratings, Imaging Spectrometry XI, Proc. of SPIE, vol. 6302, 2006, 11 pages.
Gibbons, et al., Surface-mediated alignment of nematic liquid crystals with polarized laser light, Nature, vol. 351, May 2, 1991, 1 page.
Gibbons, et al., Optically Controlled Alignment of Liquid Crystals: Devices and Applications, Molecular Crystals and Liquid Crystals, vol. 251, 1994, 19 pages.
Gibbons, et al., Optically generated liquid crystal gratings, Appl. Phys. Lett., 65, Nov. 14, 1994, 3 pages.
University of Central Florida, School of Optics CREOL PPCE, Optics in the Southeast, Technical Conference and Tabletop Exhibit, Nov. 12-13, 2003, 9 pages.
Ichimura, et al., Surface assisted photoalignment control of lyotropic liquid crystals, Part 1, Characterization and photoalignment of aqueous solutions of a water soluble dyes as lyotropic liquid crystals, J. Materials. Chem., vol. 12, 2002, abstract, 2 pages.
Ichimura, et al., Reversible Change in Alignment Mode of Nematic Liquid Crystals Regulated Photochemically by "Command Surfaces" Modified with an Azobenzene Monolayer, American Chemical Society, Langmuir, vol. 4, No. 5, 1988, 3 pages.
Zel'Dovich, et al., Devices for displaying visual information, Disclosure, School of Optics/CREOL, University of Central Florida, Jul. 2000, 10 pages.
Provenzano, et al., Highly efficient liquid crystal based diffraction grating induced by polarization holograms at the aligning surfaces, Applied Physics Letter 89, 2006, 4 pages.
Titus, et al., Efficient polarization-independent, re ective liquid crystal phase grating, Applied Physics Letter 71, Oct. 20, 1197, 3 pages.
Chen, et al. An Electrooptically Controlled Liquid-Crystal Diffraction Grating, Applied Physics Letter 67, Oct. 30, 1995, 4 pages.
Kim, et al., Unusual Characteristics of Diffraction Gratings in a Liquid Crystal Cell, Advanced Materials, vol. 14, No. 13-14, Jul. 4, 2002, 7 pages.
Pan, et al., Surface Topography and Alignment Effects in UV-Modified Polyimide Films with Micron Size Patterns, Chinese Journal of Physics, vol. 41, No. 2, Apr. 2003, 8 pages.
Fuh, et al., Dynamic studies of holographic gratings in dye-doped liquid-crystal films, Optics Letter, vol. 26, No. 22, Nov. 15, 2001, 3 pages.
Yu, et al., Polarization Grating of Photoaligned Liquid Crystals with Oppositely Twisted Domain Structures, Molecular Crystals Liquid Crystals, vol. 433, 2005, 7 pages.
Crawford, et al., Liquid-crystal diffraction gratings using polarization holography alignment techniques, Journal of Applied Physics 98, 2005, 10 pages.
Seiberle, et al., 38.1 Invited Paper: Photo-Aligned Anisotropic Optical Thin Films, SID 03 Digest, 2003, 4 pages.
Wen, et al., Nematic liquid-crystal polarization gratings by modification of surface alignment, Applied Optics, vol. 41, No. 7, Mar. 1, 2002, 5 pages.
Anagnostis, et al., Replication produces holographic optics in volume, Laser Focus World, vol. 36, Issue 3, Mar. 1, 2000, 6 pages.
Gale, Replicated Diffractive Optics and Micro-Optics, Optics and Photonics News, Aug. 2003, 6 pages.
McEldowney, et al., Creating vortex retarders using photoaligned LC polymers, Optics Letter, vol. 33, No. 2, Jan. 15, 2008, 3 pages.
Stalder, et al., Lineraly polarized light with axial symmetry generated by liquid-crystal polarization converters, Optics Letters vol. 21, No., 1996, 3 pages.
Kakichashvili, et al., Method for phase polarization recording of holograms, Sov. J. Quantum. Electron, vol. 4, No. 6, Dec. 1974, 5 pages.
Todorov, et al., High-Sensitivity Material With Reversible Photo-Induced Anisotropy, Optics Communications, vol. 47, No. 2, Aug. 15, 1983, 4 pages.
Attia, et al., Anisoptropic Gratings Recorded From Two Circularly Polarized Coherent Waves, Optics Communications, vol. 47, No. 2, Aug. 15, 1983, 6 pages.
Cipparrone, et al., Permanent polarization gratings in photosensitive langmuir blodget films, Applied Physics Letter, vol. 77, No. 14, Oct. 2, 2000, 4 pages.
Nikolova, et al., Diffraction Efficiency and Selectivity of Polarization Holographic Recording, Optica Acta: International Journal of Optics, vol. 31, No. 5, 1984, 11 pages.
Lee et al., "Generation of pretilt angles of liquid crystals on cinnamte-based photoalignment . . . ", Opt., Expr., vol. 17 (26) (Dec. 2009), abstract, 4 pages.
Yaroshchuk et al. "Azodyes as photoalignment agents for polymerizable liquid crystals", IDW'06 Digest vol. 1-3, 2006, 4 pages.
Chigrinov et al. "Anchoring properties of photoaligned azo-dye materials" Phys. Rev., E vol. 68, (Dec. 2003), 5 pages.
Pagliusi et al. Surface-induced photorefractivity in twistable nematics: toward the all-optical control of gain, Opt. Expr. vol. 16, Oct. 2008, 9 pages.
M. Honma, T. Nose, Polarization-independent liquid crystal grating fabricated by microrubbing process, Jpn. J. Appl. Phys., Part 1, vol. 42, 2003, 3 pages.
Beam Engineering for Advaced Measurements Co., et al., PCT Application No. PCT/US2016/038666 filed Jun. 22, 2016, Notification of Transmittal of the International Search Report and the Written Opinion of the International Searching Authority, or the Declaration dated Oct. 10, 2016, 16 pages.
Marrucci, et al., Pancharatnam-Berry phase optical elements for wave front shaping in the visible domain, Appl. Phys. Lett. 88, 2006, 3 pages.
Sobolewska et al., "On the inscription of period and half period surface relief gratings in azobenzene-functionalized polymers", J. Phys. Chem., vol. 112 (15) Jan. 3, 2008, 10 pages.
Barrett et al., Model of laser driven mass transport in thin films of dye-functionalized polymers, J. Chem. Phys., vol. 109 (4), Jul. 22, 1998, 13 pages.
Tabirian, U.S. Appl. No. 14/214,375, filed Mar. 14, 2014, Office Action Summary dated Jun. 27, 2017, 10 pages.
Tabirian, et al., U.S. Appl. No. 14/688,425, filed Apr. 16, 2015, Office Action Summary dated Oct. 5, 2017, 10 pages.
Serak, et al. Diffractive Waveplate Arrays [Invited], Journal of the Optical Society of America B, May 2017, pp. B56-B63, vol. 34, No. 5, 8 pages.
Emoto, Optical and Physical Applications of Photocontrollable Materials: Azobenzene-Containing and Liquid Crystalline Polymers, Polymers,Jan. 2012, 150-186, vol. 4, 38 pages.
Tabiryan, et al., Broadband waveplate lenses, Optics Express 7091, vol. 24, No. 7, Mar. 24, 2016, 12 pages.
Gerchberg, et al, practical algorithm for the determination of the phase from image and diffraction plane pictures, 1972, Optik, vol. 35, Issue 2, pp. 237-246, 10 pages.
Tabiryan, et al. Superlens in the skies: liquid-crystal-polymer technology for telescopes, Newsroom, 2016, 2 pages.
Nersisyan, et al., The principles of laser beam control with polarization gratings introduced as diffractive waveplates, Proc. of SPIE, vol. 7775, 2010, 10 pages.
Heller, A Giant Leap for Space Telescopes, Foldable Optics, S&TR, Mar. 2003, 7 pages.
Beam Engineering For Advanced Measurements Co., PCT Application No. PCT/US2015026186, The Extended European Search Report, filed on Mar. 8, 2017, 13 pages.
Blinov, et al., Electrooptic Effects in Liquid Crystal MAterials, Springer-Verlag New York, 1994, 17 pages.
Crawford, et al., Liquid Crystals in Complex Geometries; Formed by Polymer and Porous Networks, Taylor and Francis, 1996, 4 pages.

(56) References Cited

OTHER PUBLICATIONS

Honma, et al., Liquid-Crystal Fresnel Zone Plate Fabricated by Microorubbing, Japanese Journal of Applied Phsyics, vol. 44, No. 1A, 2005, 4 pages.
Tabirian, N., et al., U.S. Appl. No. 61/757,259, filed Jan. 28, 2013, 29 pages.
Vernon, J. et al., Recording Polarization Gratings with a Standing Spiral Wave, Applied Physics Letters, Oct. 2013, vol. 103, 4 pages.

* cited by examiner

POLARIZATION-INDEPENDENT SWITCHABLE LENS SYSTEM

FIELD OF THE INVENTION

This invention relates generally to the field of optics, and in particular to energized lens systems and methods of fabricating the energized lens systems with switchable and polarization-independent focal length.

BACKGROUND OF THE INVENTION

Liquid crystal materials have made it possible to fabricate devices such as retarder plates and lenses whose properties can be switched by generating an electric field. Lenses with variable or switchable focal length, based on liquid crystal materials, are well-known and used in many applications. The cost, size, weight, reliability, and lifetime of many systems that employ switchable or variable lenses based on liquid crystal materials may be reduced compared to that of similar systems in which switching or variability of optical properties is produced by physically moving conventional optical elements such as lenses and mirrors by motors and gears.

It is often the case that the optical properties of systems in which light propagates through liquid crystal materials is dependent on the polarization of the light. For example, although the focal length of lenses fabricated from traditional refractive optical materials such as glass is typically the same for any polarization, the focal length of many lenses fabricated wholly or partially from liquid crystal materials typically depends on polarization.

This difference between the properties of refractive optical systems based on traditional optical materials such as glass, and the properties of refractive optical systems based on liquid crystal materials, is due to the fact that traditional refractive optical materials are optically isotropic, whereas liquid crystal materials are typically anisotropic.

In many optical systems, sensitivity of optical properties to the polarization of light is highly undesirable. Therefore, much effort has been expended to find ways of obtaining the highly desirable features of optical systems fabricated with liquid crystal materials, including the ability to switch or vary the focal length, without incurring the disadvantage of sensitivity to polarization.

One of the design methods that has been used to create switchable lens systems for which the focal length is independent of the polarization of light is to employ two switchable liquid crystal based lenses in the switchable lens system, one of which has a shorter focal length in the off (unpowered) state than in the on (powered) state for one linear polarization of light, and the other of which has a shorter focal length in the off (unpowered) state than in the on (powered) state for the other linear polarization. With two switchable liquid crystal lenses, the overall focal length of the lens system is made to be independent of polarization in both the off (unpowered) state and the on (powered) state, and the overall focal length changes between the off (unpowered) and the on (powered) state.

Although the design method employing two switchable lenses makes it possible to create lens systems with switchable focal length, and for which the focal length in independent of polarization in both the states of the lens system, the need to have two separate switchable lenses is highly undesirable in some applications. For example, in contact lens systems with switchable focal length, the thickness of the contact lens system could be smaller if only one of the lenses comprising the contact lens system needs to be switched. Since user acceptance is sensitive to the thickness of the contact lens system, it would be highly beneficial to the viability of a contact lens design if only one switchable lens were needed, instead of two.

Thus, there is a need for an energized lens system with switchable focal length, for which the focal length is independent of the polarization of light in both of the two states of the system, and in which only one lens of the energized lens system needs to be switched in order to change the focal length of the energized lens system.

Thus, the need exists for solutions to the above problems with the prior art.

SUMMARY OF THE INVENTION

A primary object of the present invention is to provide an energized lens system of switchable focal length, for which the focal length of the energized lens system is independent of the polarization of light in both of its two states, and for which only one liquid crystal layer of the energized lens system needs to be switched in order for the focal length of the energized lens system to be switched.

A secondary object of the present invention is to provide an ophthalmic lens device of switchable focal length, for which the focal length of the ophthalmic lens device is independent of the polarization of light in both of its' two states, and for which only one liquid crystal layer of the ophthalmic lens device needs to be switched in order for the focal length of the ophthalmic lens device to be switched.

A key innovation of the present invention is the employment of a twisted nematic liquid crystal layer in the form of a lens as an element of the energized lens system or ophthalmic lens device, and in addition, to make use of the polarization transformation imposed by the twisted nematic liquid crystal layer to change the optical effects of other optical components of the energized lens system.

Alignment layers and transparent conductive layers can be provided on both boundaries of the switchable nematic liquid crystal layer so that when zero electric field is applied, the long axes of liquid crystal molecules adjacent to each alignment layer align to the axis of the alignment layer, and when an electric field is applied between the transparent conductive layers, the long axes of the liquid crystal molecules align perpendicular to the alignment layers and parallel to the electric field.

The axes of the two alignment layers can be perpendicular, resulting in a 90 degree twist in the optical axis from one of the boundaries of the layer to the other boundary. The thickness d of the liquid crystal layer can meet the Mauguin condition, described as follows:

$$d \gg \lambda/2\Delta n \tag{1}$$

In Eq. (1), $\lambda$ is the wavelength of the light transmitted through the layer, and $\Delta n$ is the birefringence of the liquid crystal filling the space between the two boundary surfaces of the layer. Both boundary surfaces of the layer are curved, and the radii of curvature of the two boundary surfaces are different so that the layer produces a focusing or defocusing effect. In general, the function of the layer is to refract light over a band of wavelengths. Because the two boundary surfaces have different curvatures, the thickness d of the layer varies with transverse position, but the Mauguin condition of Eq. (1) can be met at all transverse positions of the layer through which light is transmitted, and at all wavelengths within the operating wavelength band of the layer.

An essential benefit of inclusion of a twisted nematic liquid crystal layer in the form of a lens in the energized lens system is that application of an electric field between the transparent conductive electrodes bounding the layer, and the resulting reorientation of liquid crystal molecules in the region between these two electrodes, has two distinct effects supporting polarization-independent operation of the energized lens system.

A first such effect is that the focal length of the layer for at least one of the two linear polarizations of light is changed when the electric field is applied between the transparent conductive electrodes.

A second effect is that the polarization of light transmitted through the layer is transformed. This transformation of polarization allows an effective switching of the focal lengths of a back optical system system that follows the twisted nematic liquid crystal layer in the energized lens system or ophthalmic lens device.

The back optical system can be designed to have different focal lengths for two polarizations of light. The transformation of polarization by the twisted nematic liquid crystal layer causes switching of the focal length of the back optical system without the necessity of applying an electric field, or of incorporating any active switching mechanism in the back optical system.

Further objects and advantages of this invention will be apparent from the following detailed description of the presently preferred embodiments which are illustrated schematically in the accompanying drawings.

DETAILED DESCRIPTION OF THE INVENTION

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary of the Invention above and in the accompanying drawings, reference is made to particular features of the invention. It is to be understood that the disclosure of the invention in this specification does not include all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention can, however, be embodied in many different forms and should not be construed as limited to the embodiments set forth herein. Rather, these embodiments are provided so that this disclosure will be thorough and complete, and will convey the scope of the invention to those skilled in the art.

The present invention relates to the design and fabrication of an energized lens system with switchable focal length, with polarization-independent focal length in both its on (powered) state and its off (unpowered) state. The key improvement relative to prior art of the invention herein disclosed is that switching from its on (powered) state to its off (unpowered) state is achieved by switching a single optical element, while maintaining polarization-independent focal length in both of these states.

Figure 1:
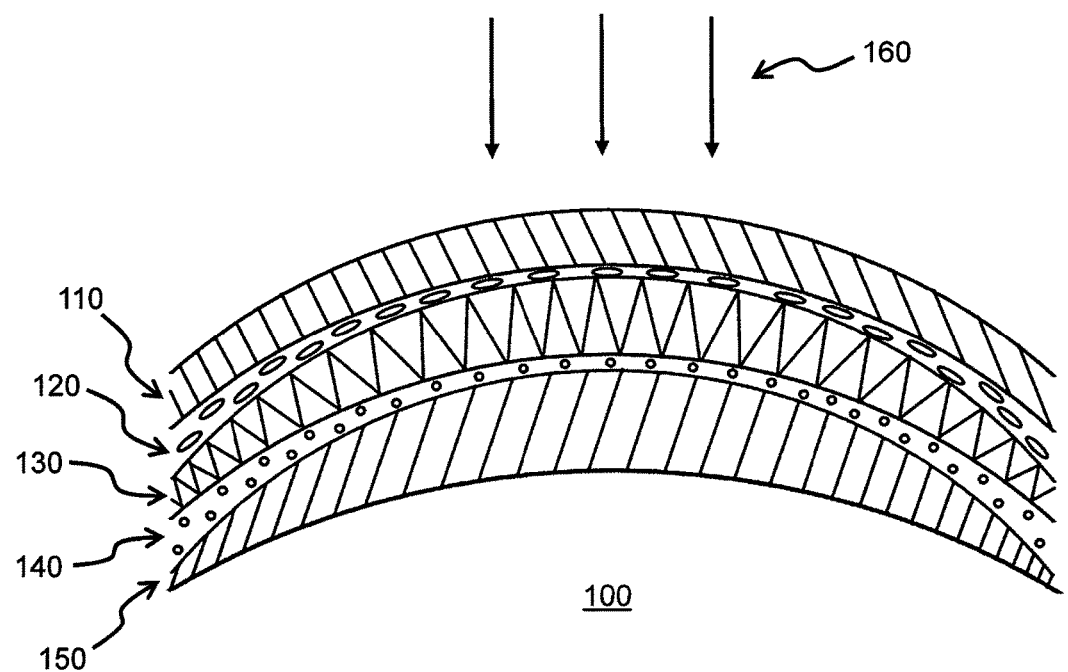
FIG. 1 illustrates a prior art side view of an optical subsystem of an energized lens system with two switchable liquid crystal layers.

One of the design methods employed in the prior art in order to achieve polarization-independent focusing with switchable focal length is illustrated in FIG. 1. The optical subsystem 100 of the energized lens system consists of a first static refractive layer 110, a first switchable liquid crystal layer 120, a second static refractive layer 130, a second switchable liquid crystal layer 140, and a third static refractive layer 150. Input light 160 from a scene, a laser, or some other optical source is incident on the optical subsystem 100 of the energized lens system.

The focal length of the energized lens system switches when both of the switchable liquid crystal layers 120 and 140 are switched between their energized and non-energized states by turning on or off an electric potential across these liquid crystal layers. The properties of all of the elements of the energized lens system are chosen such that the focal length of this system is independent of polarization in any given state, and the polarization-independent focal length of the energized lens system is different in the on (powered) state than it is in the off (unpowered) state.

In this context, the on (powered) state is the state in which an electric potential is applied across both liquid crystal layers 120 and 140, and the off (unpowered) state is the state in which zero electric potential is applied across both of these liquid crystal layers. As will become evident in the subsequent description, the optical subsystem 100 of the energized lens system is illustrated in FIG. 1 in its off (unpowered) state.

Figure 2A:
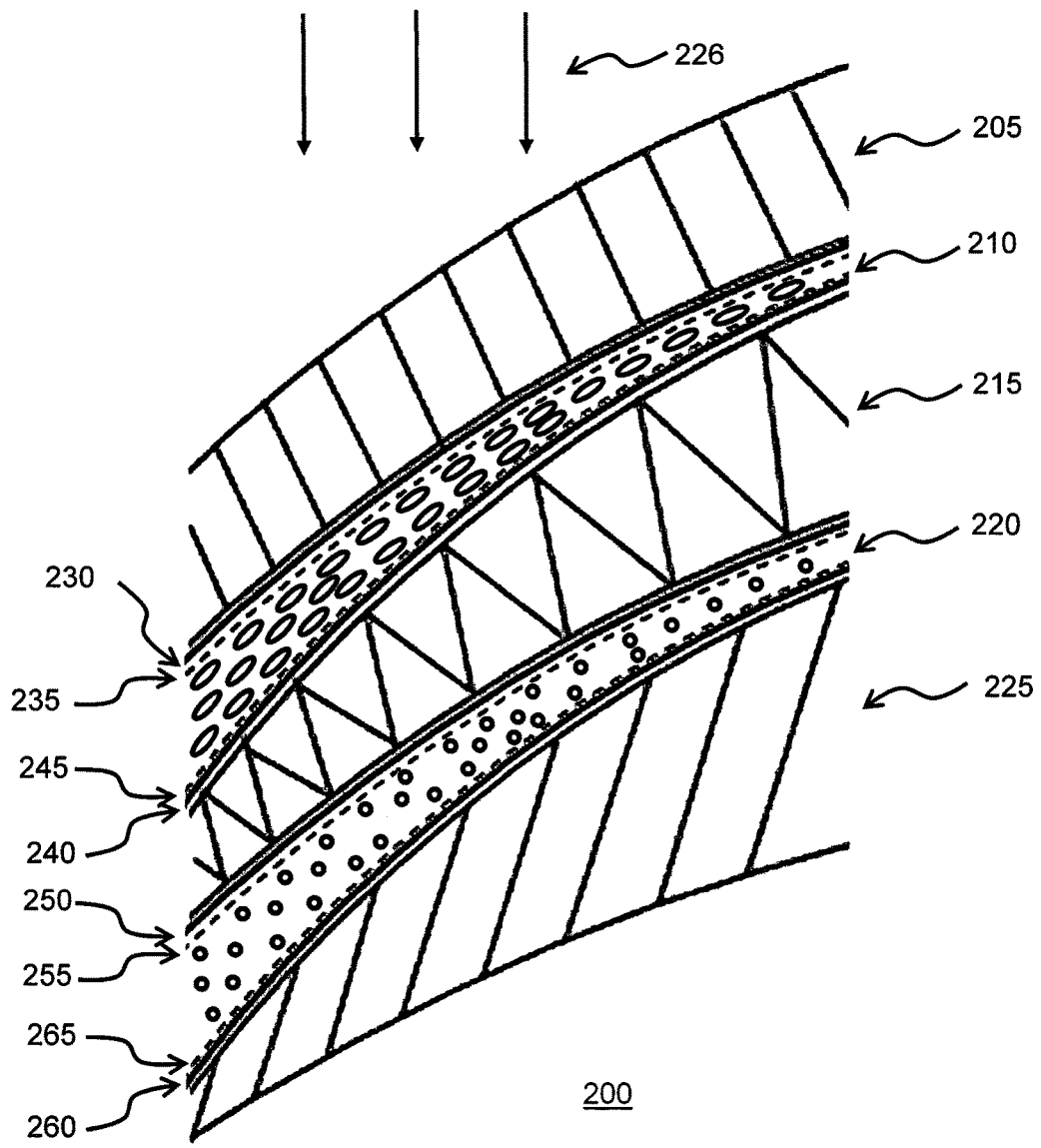
FIG. 2A illustrates an expanded view of a portion of the prior art optical subsystem of the energized lens system shown in FIG. 1 in its off (unpowered) state, that is, with the two switchable liquid crystal layers in a non-energized state.
Figure 2B:
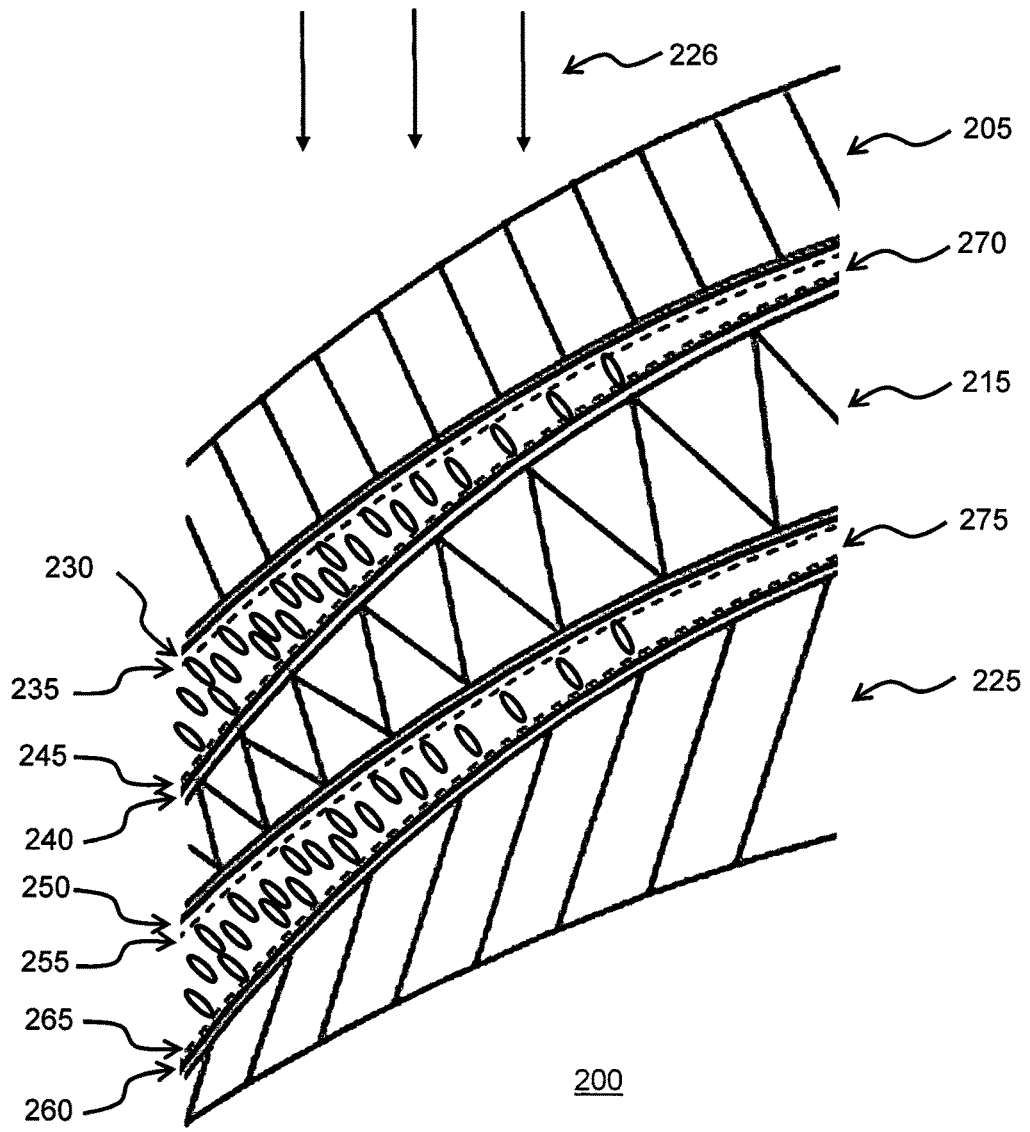
FIG. 2B illustrates an expanded view of a portion of the prior art optical subsystem of the energized lens system shown in FIG. 1 in its on (powered) state, with the two switchable liquid crystal layers in an energized state.

The details of one of the design methods employed in the prior art in order to achieve polarization-independent focusing with switchable focal length are illustrated in FIGS. 2A-2B, which show expanded views of a portion of the energized lens system illustrated in FIG. 1.

FIG. 2A shows the energized lens system of the prior art in its off (unpowered) state. FIG. 2B shows the same energized lens system in its on (powered) state. As in FIG. 1, the optical subsystem 200 of the energized lens system based on prior art shown in FIG. 2A consists of a first static refractive layer 205, a first switchable liquid crystal layer 210, a second static refractive layer 215, a second switchable liquid crystal layer 220, and a third static refractive layer 225. Light 226 from a scene, a laser, or some other optical source is incident on the energized lens system 200.

The liquid crystal layers 210 and 220 in FIG. 2A can be configured with a front curved surface and a back curved surface, with nematic liquid crystal filling the space between these two surfaces.

The back curved surface of the first static refractive layer 205 in FIG. 2A can be coated with a transparent conductive electrode 230 and an alignment layer 235. The front curved surface of the second static refractive layer 215 can be coated with a transparent conductive electrode 240 and an alignment layer 245. The back curved surface of the second static refractive layer 215 can be coated with a transparent conductive electrode 250 and an alignment layer 255. The front curved surface of the third static refractive layer 225 can be coated with a transparent conductive electrode 260 and an alignment layer 265. The alignment layers cause the adjacent liquid crystal molecules to align parallel to the axis of the alignment layer in the off (unpowered) state of the energized lens system.

In FIGS. 2A and 2B, the molecules of the liquid crystal layers (210 and 220 in FIG. 2A; 270 and 275 in FIG. 2B) are illustrated for conceptual purposes as projections onto the two-dimensional page of three-dimensional ellipsoids. Because the long axes of the liquid crystal molecules of the first switchable layer 210 are parallel to the page in FIG. 2A, representing the off (unpowered) state of the energized lens system, these molecules are represented as ellipses in FIG. 2A. Because the long axes of the liquid crystal molecules of the first switchable layer 270 are also parallel to the page in FIG. 2B, representing the on (powered) state of the energized lens system, these molecules are also represented as ellipses in FIG. 2B.

The orientation of the liquid crystal molecules in the first switchable layer rotates by 90 degrees in a plane parallel to the page between the off (unpowered) state illustrated at 210 in FIG. 2A and the on (powered) state illustrated at 270 in FIG. 2B. In the off (unpowered) state illustrated in FIG. 2A, the long axes of the liquid crystal molecules of the first switchable layer 210 are parallel to the axes of the alignment layers 235 and 245. In the on (powered) state illustrated in FIG. 2B, the long axes of the liquid crystal molecules of the first switchable layer 270 are perpendicular to the alignment layers 235 and 245.

Because the long axes of the liquid crystal molecules of the second switchable layer 220 are perpendicular to the page in FIG. 2A, representing the off (unpowered) state of the energized lens system, these molecules are represented as circles in FIG. 2A. Because the long axes of the liquid crystal molecules of the second switchable layer 275 are parallel to the page in FIG. 2B, representing the on (powered) state of the energized lens system, these molecules are represented as ellipses in FIG. 2B.

The orientation of the liquid crystal molecules in the second switchable layer rotates by 90 degrees in a plane perpendicular to the page between the off (unpowered) state are illustrated at 220 in FIG. 2A and the on (powered) state are illustrated at 275 in FIG. 2B. In the off (unpowered) state illustrated in FIG. 2A, the long axes of the liquid crystal molecules of the second switchable layer 220 are parallel to the axes of the alignment layers 255 and 265. In the on (powered) state illustrated in FIG. 2B, the long axes of the liquid crystal molecules of the second switchable layer 275 are perpendicular to the alignment layers 255 and 265.

Because of the optical anisotropy of the liquid crystal layers shown at 210 and 220 FIG. 2A, and because the liquid crystal molecules align to the axes of the alignment layers in the off (unpowered) state of the energized lens system, the focal powers of these layers are different for the two linear polarizations of light in the off (unpowered) state. The axes of the alignment layers 235 and 245, which bound liquid crystal layer 210 in FIG. 2A, are perpendicular to the axes of the alignment layers 255 and 265, which bound liquid crystal layer 220 in FIG. 2A.

This arrangement of the alignment layers makes it possible to cancel the differences in focal power of the first liquid crystal layer 210 for the two linear polarizations of light with an opposite difference in focal power of the second liquid crystal layer 220 for the two linear polarizations of light in the off (unpowered) state illustrated in FIG. 2A.

In the on (powered) state illustrated in FIG. 2B, the focal lengths of each of the two liquid crystal layers 270 and 275 are independent of the polarization, so there is no need to cancel differences in focal power for different polarizations in the on (powered) state of the energized lens system.

An example of the cancellation of focal power differences due to the anisotropic nature of nematic liquid crystal materials is as follows. For purposes of discussion, we will refer here to linearly polarized light for which the electric field is parallel to the axis of the alignment layer of the first liquid crystal layer 210 in FIG. 2A as parallel-polarized, and we will refer here to linearly polarized light for which the electric field is perpendicular to the alignment layer of the first liquid crystal layer 210 as cross-polarized.

As an example, the focal power of liquid crystal layer 210 could be −6 diopters for parallel-polarized light, and −4 diopters for cross-polarized light, for the situation in which the liquid crystal layer is in air, separated from the other refractive elements. The focal power is negative because in the example shown in FIG. 1 and FIG. 2, the liquid crystal layers are in the form of a concave lens. For this example, the axes of alignment layers 255 and 265 are perpendicular to the axes of alignment layers 235 and 245.

Provided the layer thicknesses, bounding curvatures, and liquid crystal materials are the same for liquid crystal layer 210 and liquid crystal layer 220, the focal power of liquid crystal layer 220 for parallel-polarized light is −4 diopters, and −6 diopters for cross-polarized light.

In the thin-lens approximation, the focal powers for the combination of liquid crystal layers 210 and 220 simply add, so the total focal power for the combination of liquid crystal layers 210 and 220 for both parallel-polarized and cross-polarized light is −10 diopters. Thus, the unequal focal powers of liquid crystal layer 210 for two orthogonal linear polarizations of light are compensated by an equal and opposite difference in focal powers of liquid crystal layer 220, and the combined focal power of liquid crystal layers 210 and 220 is −10 diopters for both parallel-polarized and cross-polarized light.

If the focal power of a lens system is the same for any two orthogonal polarizations, then it is the same for any polarization. The axes defined above for parallel-polarized and cross-polarized light are orthogonal. Therefore, since the combined focal power of liquid crystal layers 210 and 220 is −10 diopters for both parallel-polarized and cross-polarized light, it is −10 diopters for light of any polarization.

For the example above, in the on (powered) state illustrated in FIG. 2B of the energized lens system, the focal power for both parallel-polarized and cross-polarized light will be −8 diopters. If the combined focal power in air of the first static refractive layer 205 and the second static refractive layer 215 is +10 diopters in both the off (unpowered) and on (powered) states of the energized lens system, and again using the thin-lens approximation under which the focal power in air of a series of optical elements is approximated as the sum of the focal powers in air of the individual elements, then the total focal power for the prior art energized lens system is zero in the off (unpowered) state illustrated in FIG. 2A, and +2 diopters in the on (powered) state illustrated in FIG. 2B, and these focal powers are independent of the polarization state of the incident light.

An exemplary list of focal powers of all the layers of the energized lens system illustrated in FIGS. 2A-2B is provided in Table 1. As noted, the total optical power is zero for both parallel-polarized and cross-polarized light when the energized lens system is in the off (unpowered) state, that is, with the fields between the pair of transparent conductive coatings 230, 240 and the pair of transparent conductive coatings 250, 260 are both set to zero.

Also as noted, the total optical power is +2 diopters for both parallel-polarized and cross-polarized light when the energized lens system is in the on (powered) state, that is, with the fields between the pair of transparent conductive coatings 230, 240 and pair of transparent conductive coatings 250, 260 both non-zero, with a sufficient amplitude and appropriate modulation waveform to switch the corresponding liquid crystal (LC) layers.

Table 1 shows the optical powers in diopters of the first LC layer (210 in FIG. 2A, 270 in FIG. 2B), of the second LC layer (220 in FIG. 2A, 275 in FIG. 2B), and of all other optical elements of the energized lens system with optical power (205, 215, and 225 in FIG. 2A and FIG. 2B) combined. For purposes of illustration, the optical powers are listed for the individual optical elements in air, and the thin-lens approximation is used to allow simple addition of the individual optical powers in order to obtain the total optical power shown in Table 1.

TABLE 1

Focal powers (in diopters) of optical elements of energized lens system illustrated in FIGS. 2A-2B

| State and input polarization | 1st LC layer | 2nd LC layer | All other | Total |
|---|---|---|---|---|
| Off state, parallel polarization | −6 | −4 | +10 | 0 |
| Off state, cross polarization | −4 | −6 | +10 | 0 |
| On state, parallel polarization | −4 | −4 | +10 | +2 |
| On state, cross polarization | −4 | −4 | +10 | +2 |

The prior art design method illustrated in FIGS. 2A-2B for an energized lens system has the advantage that the anisotropic nature of the nematic liquid crystal used to switch the focal length is compensated in such a way that the focal length is the same for any polarization of light, whether the energized lens system is in the off (unpowered) state or the on (powered) state. However, this prior art design has the disadvantage that two separate switchable elements are required in order to achieve polarization-independent focal power in both states of the energized lens system.

According to the present invention, it is possible to eliminate one of the liquid crystal layers of the prior art design method illustrated in FIGS. 2A-2B, yet retain the ability to switch between two states, in both of which the focal length for light incident on the energized lens system is independent of the polarization of the light. Additionally, by use of the technology of diffractive waveplates, which provide focusing of light by a coating only a few micrometers in thickness, it is possible in the present invention to provide all the functionality of the prior art design illustrated in FIGS. 2A-2B in a structure approximately half as thick. This difference in required thickness can make the difference between a viable design and a non-viable design in applications in which thickness is a critical parameter, such as in the design of contact lenses or other ophthalmic lens device of switchable focal length.

Figure 3:
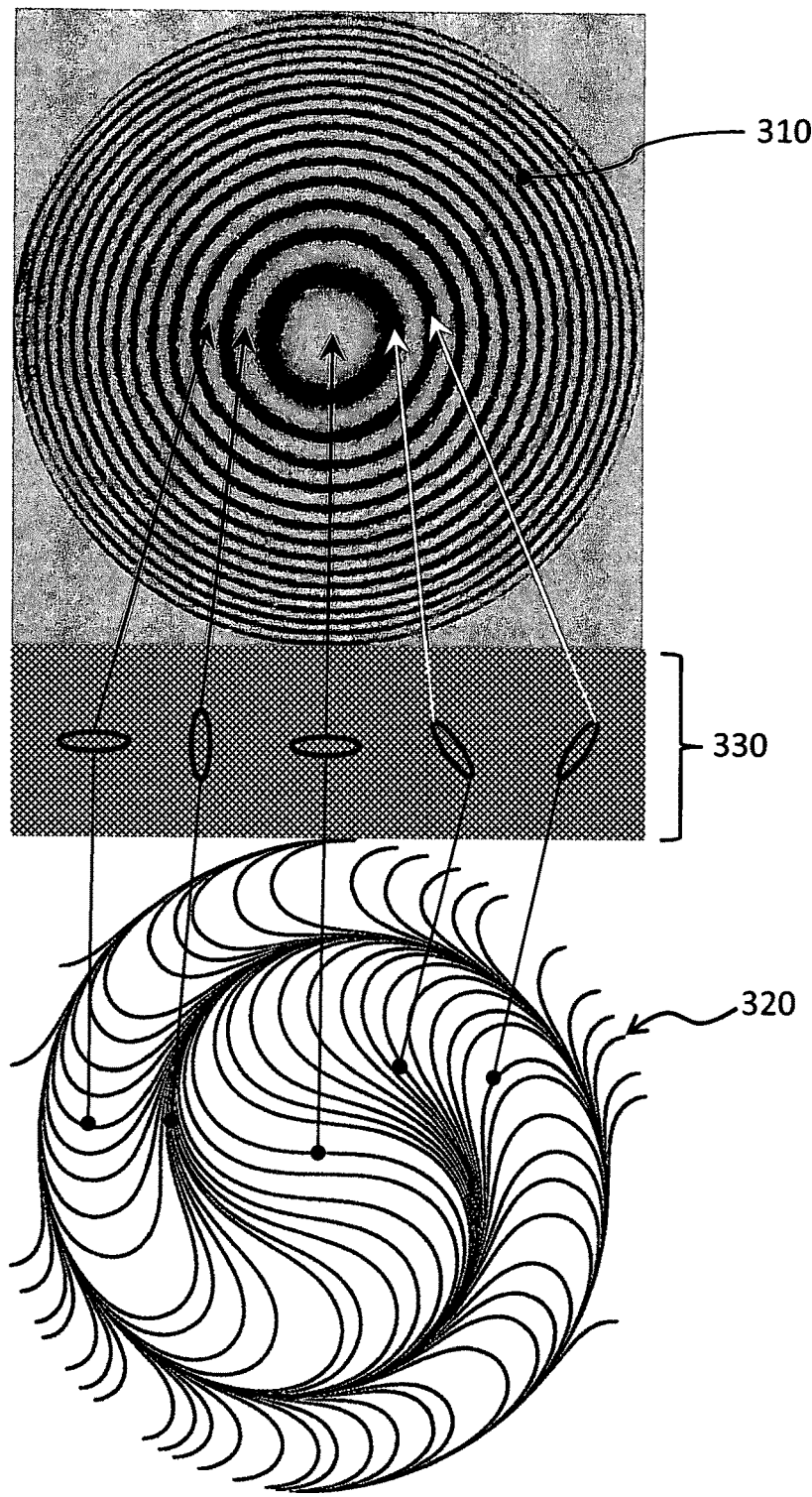
FIG. 3 illustrates a prior art view of a diffractive waveplate coating with lensing properties.

An example of a diffractive waveplate coating with lensing properties from prior art is illustrated in FIG. 3. A photograph of such a coating between crossed polarizers is shown at 310, an illustration of the optical axis pattern of such a coating is shown at 320, and the local orientations of liquid crystal polymer molecules comprising the coating are shown at 330.

Figure 4A:
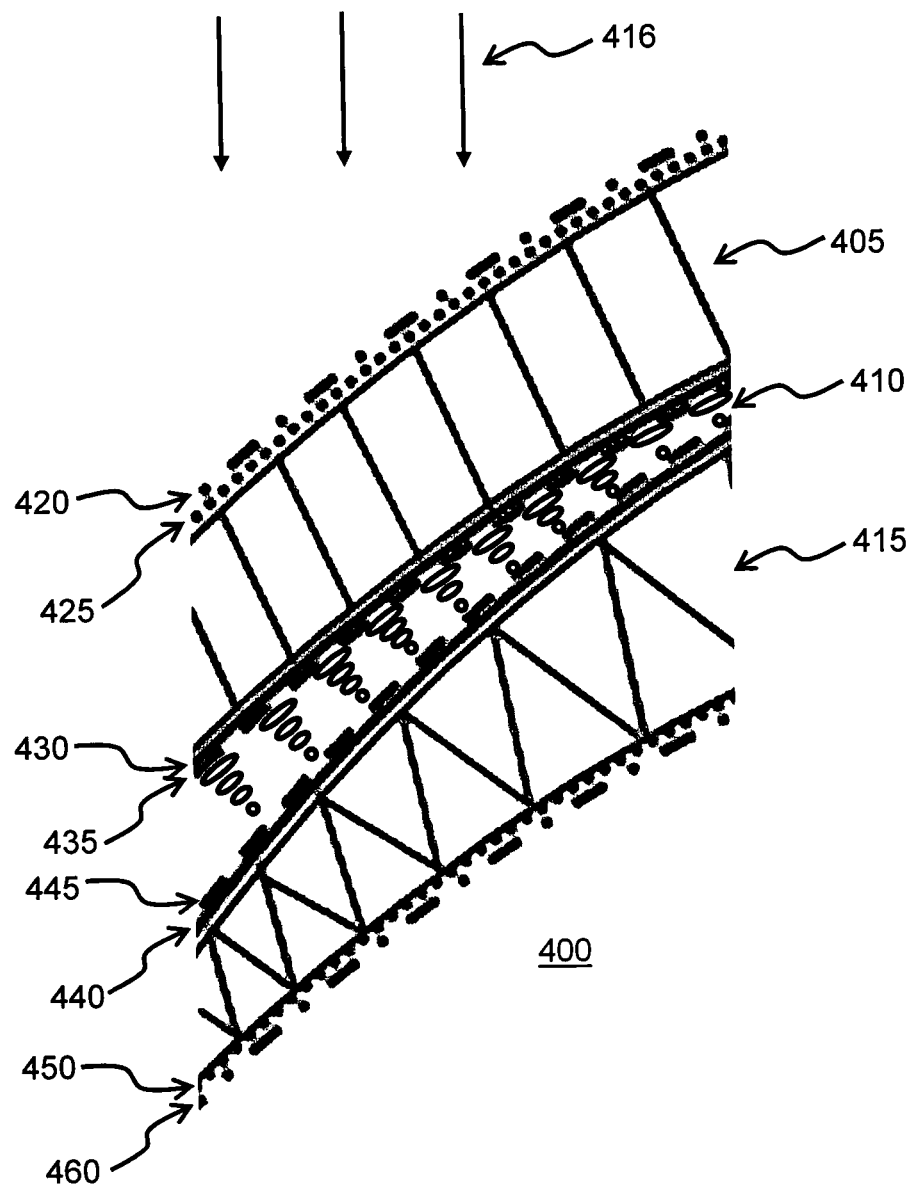
FIG. 4A illustrates an exemplary embodiment of the optical subsystem of an energized lens system of the present invention in its off (unpowered) state, with a single switchable twisted nematic liquid crystal layer in a non-energized state, and with a polarization converter combined with a diffractive waveplate coating with lensing properties performing the function of the back optical system.
Figure 4B:
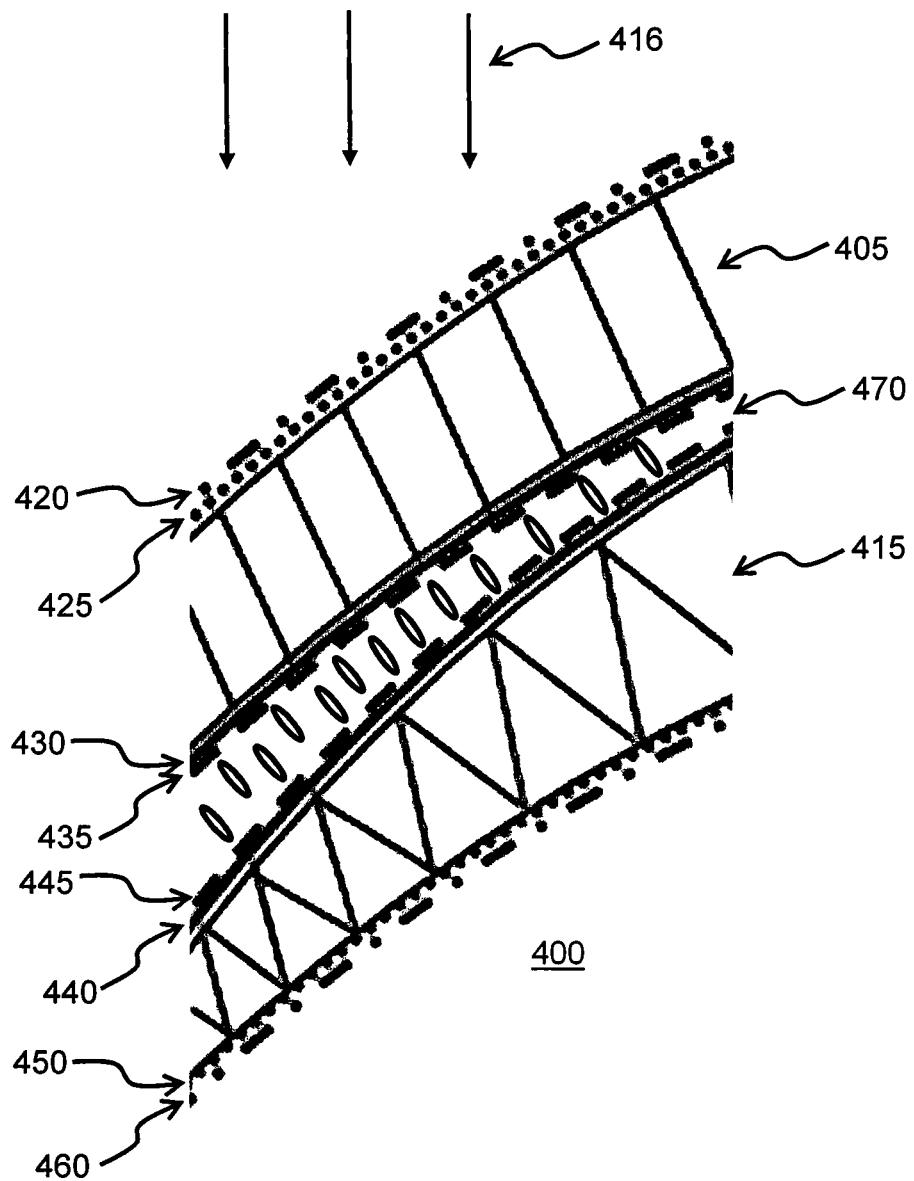
FIG. 4B illustrates an exemplary embodiment of the optical subsystem of an energized lens system of the present invention in its on (powered) state, with a single switchable twisted nematic liquid crystal layer in its energized state, and with a polarization converter combined with a diffractive waveplate coating with lensing properties performing the function of the back optical system.

An exemplary embodiment of the present invention is illustrated in FIGS. 4A-4B, in which the advantage of switchable and polarization-independent focal power is achieved, but with only a single switchable nematic liquid crystal layer, two coatings for polarization conversion, and two diffractive waveplate coatings with lensing properties.

FIG. 4A shows the optical subsystem 400 of the energized lens system of the present invention in its off (unpowered) state.

FIG. 4B shows the same energized lens system in its on (powered) state. Major elements of the optical subsystem 400 of the energized lens system in FIG. 4A include a first static refractive layer 405, a twisted nematic liquid crystal layer 410, and a second static refractive layer 415.

Incident light 416 encounters, in the following order, the following elements with refractive power, polarization conversion capability, or both: a first diffractive waveplate coating with lensing properties 420, a first polarization conversion coating 425, a first static refractive layer 405, a twisted nematic liquid crystal layer 410, a second static refractive layer 415, a second polarization conversion coating 450, and a second diffractive waveplate coating with lensing properties 460.

The back curved surface of the first static refractive layer 405 can be coated with a transparent conductive electrode 430 and an alignment layer 435. The front curved surface of the second static refractive layer 415 can be coated with a transparent conductive electrode 440 and an alignment layer 445. The alignment layers cause the adjacent liquid crystal molecules of the twisted nematic liquid crystal layer 410 to align parallel to the axes of the alignment layers 435 and 445 in the off (unpowered) state of the energized lens system.

Comparing FIG. 2A, illustrating an energized lens system based on prior art in the off (unpowered) state, and FIG. 4A, illustrating an exemplary embodiment of an energized lens system of the present invention in the off (unpowered state), it is evident that in the prior art energized lens system, the axes of the alignment layers are so arranged that the axes of the liquid crystal molecules at the two bounding surfaces of the liquid crystal layer 210 are parallel.

In the energized lens system of the present invention, the axes of the alignment layers 435 and 445 are so arranged that the axes of the liquid crystal molecules at the two bounding surfaces of the twisted nematic liquid crystal layer 410 are perpendicular. The term "twisted" refers to the rotation, or twisting, of the liquid crystal axis as one proceeds from one boundary of the twisted nematic layer to the other boundary. It will be assumed that the thickness of the liquid crystal layer 410 in FIG. 4A satisfies the Mauguin condition given by Eq. (1) for the entire optical zone over which light is incident, and for all wavelengths of interest.

The key to the polarization independence of focal length in both the off (unpowered) state illustrated in FIG. 4A and in the on (powered) state shown in FIG. 4B of the exemplary energized lens system of the present invention is the transformation of polarization by the various constituents of this system in both the off and on states.

In the illustration in FIG. 4A of the optical subsystem 400 of the energized lens system of the present invention in the off (unpowered) state, light 416 that is left-hand circularly polarized (LHCP) at the input to coating 420 can be transformed by the coating 420 to right-hand circularly polarized (RHCP), by coating 425 to parallel-polarized, by twisted nematic liquid crystal layer 410 to cross-polarized, to RHCP by coating 450, and back to LHCP by coating 460.

Similarly, in the illustration in FIG. 4A of the optical subsystem 400 of the energized lens system of the present invention in the off (unpowered) state, light 416 that is RHCP at the input to coating 420 can be transformed by the coating 420 to LHCP, by the coating 425 to cross-polarized, by twisted nematic liquid crystal layer 410 to parallel-polarized, to LHCP by the coating 450, and to RHCP by the coating 460.

In the illustration in FIG. 4B of the optical subsystem 400 of the energized lens system of the present invention in the on (powered) state, light that is LHCP at the input to the coating 420 can be transformed by coating 420 to RHCP, and by the coating 425 to parallel-polarized. In the on (powered) state, the twisted nematic liquid crystal layer 470 in FIG. 4B has no effect on polarization, so light that is parallel-polarized at the input side of the layer, the side with the coatings 430 and 435 in FIG. 4B, is still parallel-polarized at the output side of this layer, i.e. the side with the coatings 440 and 445 in FIG. 4B.

This parallel-polarized light can then be transformed to LHCP by the coating 450, and to RHCP by the coating 460. Similarly, in the illustration in FIG. 4B of the optical subsystem 400 of the energized lens system of the present invention in the on (powered) state, light that is RHCP at the input to the coating 420 can be transformed by the coating 420 to LHCP, and by the coating 425 to cross-polarized.

In the on (powered) state, the twisted nematic liquid crystal layer 470 in FIG. 4B has no effect on polarization, so light that is cross-polarized at the input side of the layer, the side with the coatings 430 and 435 in FIG. 4B, is still cross-polarized at the output side of this layer, i.e. the side with coatings 440 and 445 in FIG. 4B. This cross-polarized light can then be transformed to RHCP by the coating 450, and to LHCP by coating 460. All of these polarization transformations are summarized in Table 2.

The only function of the first liquid crystal layer in FIGS. 2A-2B that supports switching of the focal length of the energized lens system 200 is to change its focal length for one linear polarization upon application of an electric field between transparent conductive coatings 230 and 240. Such a change in focal length is due to the change in orientation of the liquid crystal molecules comprising that layer from the orientation shown at 210 in FIG. 2A to the orientation shown at 270 in FIG. 2B.

TABLE 2

Polarization transformations of light in FIG. 4A and FIG. 4B

| | FIG. 4A, off state | | FIG. 4B, on state | |
|---|---|---|---|---|
| Input polarization: | LHCP | RHCP | LHCP | RHCP |
| Polarization at output of each element: | | | | |
| Diffractive lens coating 420 | RHCP | LHCP | RHCP | LHCP |
| Conversion coating 425 | parallel | crossed | parallel | crossed |
| Liquid crystal layer 410 | crossed | parallel | N/A | N/A |
| Liquid crystal layer 470 | N/A | N/A | parallel | crossed |
| Conversion coating 450 | RHCP | LHCP | LHCP | RHCP |
| Diffractive lens coating 460 | LHCP | RHCP | RHCP | LHCP |

Switching of the liquid crystal layer from the configuration 210 to the configuration of 270 does not affect the property of the layer that light that is parallel-polarized at the input to the layer is still parallel-polarized at the output from the layer, and light that is cross-polarized at the input to the layer is still cross-polarized at the output from the layer.

A critical innovation of the present invention is that the twisted nematic form of the liquid crystal layer illustrated at 410 in FIG. 4A performs two distinct functions that support switching of the focal length of the optical subsystem 400 of the energized lens system. The first of these functions is, as in the case of the first liquid crystal layer in FIGS. 2A-2B, to change focal length upon application of an electric field. The second of these functions performed in the twisted nematic liquid crystal layer 410 of the exemplary energized lens system of the present invention, illustrated in FIGS. 4A-4B, but not in the first liquid crystal layer 210 of the exemplary prior art system, illustrated in FIGS. 2A-2B, is the function of transforming the polarization of light transmitted through this liquid crystal layer.

Parallel-polarized light incident on the first liquid crystal layer 210 in FIG. 2A exits the layer with the same polarization, but as shown in Table 2, parallel polarized light incident on the twisted nematic liquid crystal layer 410 in FIG. 4A is cross-polarized upon exiting the layer. Similarly, cross-polarized light incident on the first liquid crystal layer 210 in FIG. 2A exits the layer with the same polarization, but cross-polarized light incident on the twisted nematic liquid crystal layer 410 in FIG. 4A is parallel-polarized upon exiting the layer. This polarization transformation must occur because of the 90 degree twist angle of the twisted nematic layer 410, and because of the assumption that the thickness d of the layer is sufficient to satisfy the Mauguin condition of Eq. (1).

The achievement of switchable, polarization-independent focusing using the design of FIG. 4 can be explained by reference to Table 3. In this table, which applies to the exemplary embodiment of the present invention illustrated in FIG. 4, the leftmost column shows the four possible combinations of the state of the energized lens system and the input circular polarization. The two possible states are on (unpowered) and off (powered). The two possible states of input polarization are LHCP and RHCP. The optical powers in diopters given in the body of the table are the optical powers for the input light polarization shown in the leftmost column, i.e. the polarization at the input to the coating 420 in FIG. 4A and FIG. 4B, even though (as indicated in Table 2) the polarization changes as light propagates through the energized lens system.

The column labeled "1st DW coating" in Table 3 shows the optical power of the diffractive waveplate coating with lensing properties 420 in FIG. 4A and FIG. 4B. The column labeled "LC layer" in Table 3 shows the optical power of the twisted nematic liquid crystal layer 410 in FIG. 4A and 470 in FIG. 46. The column labeled "2nd DW coating" in Table 3 shows the optical power of the diffractive waveplate coating with lensing properties 460 in FIG. 4A and FIG. 4B. The column labeled "All other" in Table 3 shows the optical power of all the other optical elements with optical power in FIG. 4A and FIG. 4B, which consist of the two static refractive layers 405 and 415.

For purposes of illustration, the optical powers are listed in Table 3 for the individual optical elements in air, and the thin-lens approximation is used to allow simple addition of the individual optical powers in order to obtain the total optical power shown in Table 3.

TABLE 3

Focal powers (in diopters) of optical elements of energized lens system illustrated in FIG. 4

| State and input polarization | 1st DW coating | LC layer | 2nd DW coating | All other | Total |
|---|---|---|---|---|---|
| Off state, LHCP | +1 | −12 | +1 | +10 | 0 |
| Off state, RHCP | −1 | −8 | −1 | +10 | 0 |
| On state, LHCP | +1 | −8 | −1 | +10 | +2 |
| On state, RHCP | −1 | −8 | +1 | +10 | +2 |

The value of the present invention is due to the change in sign of the optical powers listed in the column labeled "2nd DW coating" in Table 3, for either circular polarization at the input to the energized lens system of FIG. 4, between the off (unpowered) state and the on (powered) state.

For example, the optical power shown in Table 3 for the "2nd DW coating", i.e. diffractive waveplate coating with lensing properties 460 in FIG. 4A and FIG. 4B, for LHCP polarization of the incident light 416 at the input coating 420, is given in Table 3 as +1 diopters in the off (unpowered) state of the energized lens system, and as −1 diopters in the on (powered) state of the energized lens system.

Similarly, the optical power shown in Table 3 for the "2nd DW coating", i.e. diffractive waveplate coating with lensing properties 460 in FIG. 4A and FIG. 4B, for RHCP polarization of the incident light 416 at the input coating 420, is given in Table 3 as −1 diopters in the off (unpowered) state of the energized lens system, and as +1 diopters in the on (powered) state of the energized lens system.

There are two factors which explain these changes in sign of the focal length of the diffractive waveplate coating with lensing properties. First, as is well known in the art, the sign of the focal length of any diffractive waveplate coating with lensing properties for LHCP light is opposite to the sign of its focal length for RHCP light. Second, as indicated in Table 2, for any given circular polarization of the incident light 416 to the optical subsystem 400 of the energized lens system, the circular polarization that is incident on the diffractive waveplate coating with lensing properties 460 changes between the off (unpowered) state of the energized lens system illustrated in FIG. 4A and the on (powered) state of the energized lens system illustrated in FIG. 4B.

Specifically, as indicated in Table 2, for LHCP incident light 416 to the optical subsystem 400 of the energized lens system, the light incident on the diffractive waveplate coating with lensing properties 460 is RHCP when the energized lens system is in the off (unpowered) state, and LHCP when the energized lens system is in the on (powered) state. Similarly, as indicated in Table 2, for RHCP incident light 416 to the optical subsystem 400 of the energized lens system, the light incident on the diffractive waveplate coating with lensing properties 460 is LHCP when the energized lens system is in the off (unpowered) state, and RHCP when the energized lens system is in the on (powered) state.

These reversals of the circular polarization at the input to the diffractive waveplate coating with lensing properties 460 are due to the fact that the liquid crystal layer 410 in FIG. 4A, illustrating the off (unpowered) state of the energized lens system, changes the polarization of light transmitted through the layer due to its 90 degree twist structure. But this same liquid crystal layer shown at 470 in FIG. 4B, illustrating the on (powered) state of the energized lens system, does not change the polarization of light transmitted through the layer because the application of an electric field eliminates the twisted structure of the liquid crystal layer.

Comparing Tables 1 and 3, in both cases the total optical power in the off (unpowered) state is zero, and the total optical power in the on (powered) state is +2 diopters, regardless of polarization. An important distinction between the prior art case for which focal powers are shown in Table 1, and the exemplary embodiment of the present invention for which focal powers are shown in Table 3, is that switching the energized lens system based on the prior art design requires the application of an electric field across two liquid crystal layers, as illustrated in FIG. 2A and FIG. 2B. Switching the energized lens system of the present invention requires application of an electric field across only a single liquid crystal layer, as illustrated in FIG. 4A and FIG. 4B.

As noted previously, if the focal length of a lens system is the same for any orthogonal pair of polarization states, then the focal length of the lens system is the same for any polarization state. Therefore, the fact that the energized lens system for which focal powers are shown in Table 1 has a focal power of zero for both parallel polarization and crossed polarization in the off (unpowered) state of the energized lens system implies that it has a focal power of zero for light of any polarization because the parallel-polarized and cross-polarized polarization states are orthogonal.

The fact that the energized lens system for which focal powers are shown in Table 1 has a focal power of +2 diopters for both parallel polarization and crossed polarization in the on (powered) state of the energized lens system implies that it has a focal power of +2 diopters for light of any polarization.

The fact that the energized lens system for which focal powers are shown in Table 3 has a focal power of zero for incident light of both LHCP and RHCP in the off (unpowered) state of the energized lens system implies that it has a focal power of zero for light of any polarization because the LHCP and RHCP polarization states are orthogonal. The fact that for the energized lens system for which focal powers are shown in Table 3 has a focal power of +2 diopters for both LHCP and RHCP in the on (powered) state of the energized lens system implies that it has a focal power of +2 diopters for light of any polarization.

As is well known in the art, one of the types of coatings that converts light back and forth between linear polarization and circular polarization is the quarter-wave coating, a coating that has one-quarter wave of retardation difference between two orthogonal linear polarizations of light. As is also well known in the art, methods are available to fabricate coatings often referred to as broadband quarter-wave coatings which have very close to one quarter wave of retardation difference for two orthogonal linear polarizations of light over a broad band of optical wavelengths, thereby achieving a high degree of efficiency in this polarization conversion over such broad bands of wavelength. The polarization conversion coatings 425 and 450 in the exemplary embodiment of the present invention illustrated in FIG. 4A and FIG. 4B can be such quarter-wave coatings or broadband quarter-wave coatings.

As is well known in the art, diffractive waveplate coatings, for example diffractive waveplate coatings with lensing properties, have diffraction efficiency close to 100% when the optical retardation imposed by the coating is one-half wave. As is also well known in the art, methods are available to fabricate diffractive waveplate coatings often referred to as broadband half-wave coatings which have very close to one half wave of retardation difference for two orthogonal linear polarizations of light over a broad band of optical wavelengths, thereby achieving a high degree of diffraction efficiency over such broad bands of wavelength. The diffractive waveplate coatings with lensing properties 420 and 460 in the exemplary embodiment of the present invention illustrated in FIG. 4A and FIG. 4B can be such half-wave coatings or broadband half-wave coatings.

GLOSSARY

In the description and claims directed to the presented invention, various terms can be used for which the following definitions can apply:

Alignment layer: refers to a layer adjacent to a liquid crystal layer that influences and aligns the orientation of molecules within the liquid crystal layer. Typically, alignment layers cover the surfaces bounding a nematic liquid crystal layer. The microstructure of the alignment layer defines an axis, and intermolecular forces between the liquid crystal molecules and the alignment layer cause the director axis of the nematic liquid crystal to align parallel to the alignment layer.

Back: refers to the order in which light encounters optical elements in an optical system. For example, the back surface of any optical element is that surface that is the last surface of that optical element encountered by light that is propagating through the optical system in the direction expected in normal operation of the optical system.

Back optical system: refers to a portion of the optical subsystem of an energized lens system. The back optical system can consist of one or more static (non-switching) refractive layers, the static refractive layers comprised of isotropic dielectric material, and one or more static (non-switching) layers with polarization-sensitive focusing properties. The surfaces bounding the back optical system, or contained within the back optical system, can generally have curvature, resulting in optical refractive power. The back optical system, if placed in air, would have optical powers that are different for different polarizations of light.

Diffractive waveplate coating with lensing properties: refers to a coating on a dielectric material, the coating consisting of an anisotropic dielectric material, the optical retardation produced by the coating being generally one-half wave at the center of an operating wavelength band or over the entire band of wavelengths for which the coating is designed to operate, the optical axis angle of the anisotropic dielectric material varying generally with a quadratic dependence on the distance from the center of the coated optic, such that the coating focuses one circular polarization of light and defocuses the other circular polarization of light. The coating can be applied to either a flat or a curved surface.

Energized state: refers to the condition of a nematic liquid crystal layer in which an electric field with an amplitude sufficient to re-orient the molecules of liquid crystal is applied. The electric field can be constant in time or may alternate polarity at a rate compatible with the liquid crystal material.

Energized lens system: refers to a lens system which can be in either an energized state or a non-energized state, and which consists of a controller and an optical subsystem. The controller consists of a source of electric potential, the means to connect the source of electric potential to transparent conductive coatings that are part of the optical subsystem, and the capability to set the applied electric potential to either zero or to a direct-current or alternating current magnitude that is sufficient to reorient the liquid crystals across which the electric potential is applied.

Front: refers to the order in which light encounters optical elements in an optical system. For example, the front surface of any optical element is that surface that is the first surface of that optical element encountered by light that is propagating through the optical system in the direction expected in normal operation of the optical system.

Front optical system: refers to the portion of the optical subsystem of an energized lens system onto which outside light is incident in the normal operation of the energized lens system. The front optical system can consist of one or more static (non-switching) refractive layers, the static refractive layers comprised of isotropic dielectric material, and one or more static (non-switching) layers with polarization-sensitive focusing properties. The surfaces bounding the front optical system, or contained within the front optical system, can generally have curvature, resulting in optical refractive power. The front optical system, if placed in air, would have optical powers that are different for different polarizations of light.

Liquid crystal: refers to a state of matter having properties between a conventional liquid and a solid crystal. A liquid crystal cannot be characterized as a solid but its molecules exhibit some degree of alignment. The orientation of the molecules of a liquid crystal can be manipulated by external forces, for example, the intermolecular forces due to interaction of the liquid crystal with a nearby alignment layer, and the presence of an electric field.

Off (unpowered) state: refers to the state of an energized lens system in which a zero electric field is applied to all switchable liquid crystal layers included within the energized lens system.

On (powered) state: refers to the state of an energized lens system in which a non-zero electric field is applied across at least one liquid crystal layer, the field amplitude and its temporal dependence being sufficiently large so as to orient the molecules parallel to the electric field within the liquid crystal layer or layers across which the electric field is applied.

Ophthalmic lens device: refers to any optical device used to correct human vision, and that resides near, on, or in the human eye. Ophthalmic lens devices include at least spectacles, contact lenses, and intraocular lenses.

Optical subsystem: refers to the optical portion of an energized lens system. The optical subsystem consists of a front optical system, a switchable twisted nematic liquid crystal layer, and a back optical system. In the normal operation of the energized lens system, optical radiation is incident on the front optical system, and propagates through the optical system in the following order: front optical system, switchable twisted nematic liquid crystal layer, back optical system.

Optical zone: refers to the clear aperture of an optical component, or to an area of an ophthalmic lens device through which a wearer of the ophthalmic lens device sees.

Polarization conversion coating: refers to a coating that converts light from one polarization state to another polarization state. The polarization coating may be in the form of a coating that produces an optical retardation of generally one-quarter wave at the center of an operating wavelength band, or over an entire operating wavelength band. The polarization coating may consist of a layer of anisotropic dielectric material with an optical axis orientation that is uniform over the optical zone or clear aperture of the coating.

Static refractive layer: refers to an optical component of an energized lens system. The static refractive layer is comprised of an isotropic dielectric material and has curved surfaces that can result in non-zero optical power. The static refractive layer has the same optical properties whether the energized lens system is in its off (unpowered) state or its on (powered) state.

Switchable liquid crystal layer: refers to a layer of nematic liquid crystal which is an optical component of an energized lens system. The switchable liquid crystal layer is bounded by curved surfaces which are coated with alignment layers and transparent conductive coatings.

Twisted nematic liquid crystal layer: refers to a layer of nematic liquid crystal configured such that when no electric field is applied, the long axes of the liquid crystal align to the axes of the alignment layers provided on the boundaries of the layer, and such that the axes of the bounding alignment layers are perpendicular to each other.

ALTERNATIVE EMBODIMENTS

While FIGS. 4A-4B are useful in describing an exemplary embodiment of the present invention, the invention is capable of other embodiments. Also, FIGS. 4A-4B show only the optical subsystem of the present invention, and do not illustrate the controller which can apply either a zero electric field or a non-zero electric field across the transparent conductive electrode coatings bounding the nematic liquid crystal layer 410 in FIG. 4A and 470 in FIG. 4B.

Figure 5:
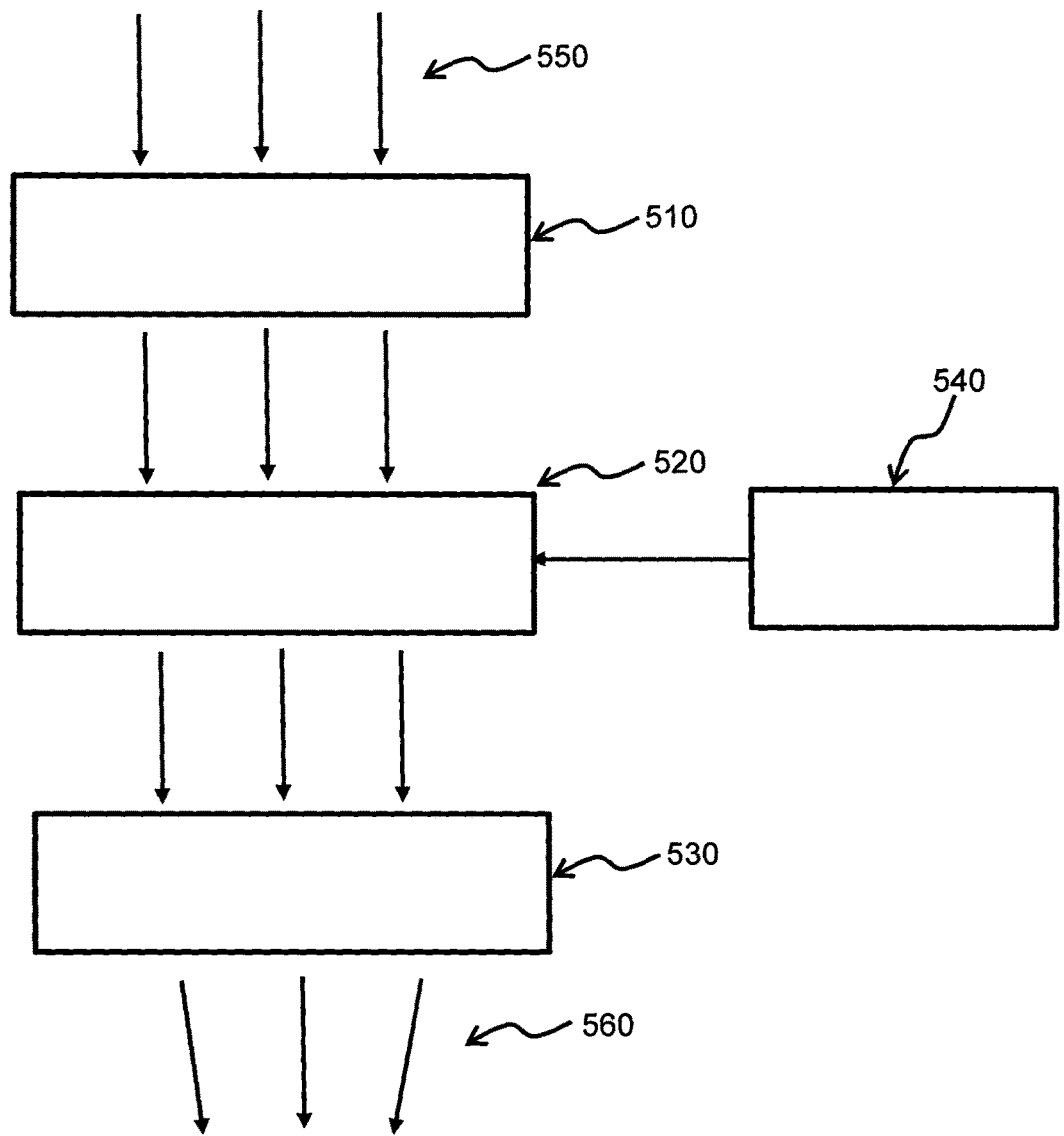
FIG. 5 illustrates the overall layout of an energized lens system of the present invention using the optical subsystem of FIGS. 4A-4B.

FIG. 5 shows a generalized embodiment of the energized lens system of the present invention, consistent with the exemplary embodiment illustrated in FIGS. 4A-4B. This generalized embodiment 500 of the energized lens system of the present invention consists of a front optical system 510, a twisted nematic liquid crystal layer 520, a back optical system 530, and a controller 540.

For purposes of illustration, incident light 550 enters the energized lens system at the front optical system 510 and exits the energized system at 560, after the back optical system 530. The controller 540 can be used to switch the state of the energized lens system 500 between its energized state and its non-energized state by applying either a zero or non-zero electric field across the twisted nematic liquid crystal layer 520. The switching of the nematic liquid crystal layer 520 has two critical and independent effects, which are to change the focal length of the nematic liquid crystal layer 520, and to transform the polarization of light propagated through the layer.

The back optical system 530 has different focal lengths for different polarizations of light. The combination of these two independent effects of switching the twisted nematic liquid crystal layer between its energized and its non-energized state results in polarization-independent focal length in both states, and in a different focal length for each of the two states.

In the exemplary embodiment of the present invention illustrated in FIGS. 4A-4B, the role of the front optical system 510 in FIG. 5 is supplied by the diffractive waveplate coating with lensing properties 420, the polarization conversion coating 425, and the first static refractive layer 405.

In the exemplary embodiment of the present invention illustrated in FIGS. 4A-4B, the role of the twisted nematic liquid crystal layer 520 in FIG. 5 is supplied by the twisted nematic liquid crystal layer 410 in FIG. 4A and 470 in FIG. 4B, including the transparent conductive coatings 430 and 440, and the alignment layers 435 and 445.

In the exemplary embodiment of the present invention illustrated in FIGS. 4A-4B, the role of the back optical system 530 in FIG. 5 is supplied by the second static refractive layer 415, the polarization conversion coating 450, and the diffractive waveplate coating with lensing properties 460. The front and back optical systems, both in the exemplary embodiment illustrated in FIGS. 4A-4B and in the generalized embodiment illustrated in FIG. 5, include static refractive layers with curved surfaces and a means of focusing light such that the focal lengths are different for two different polarizations.

In the exemplary embodiment illustrated in FIGS. 4A-4B, polarization-dependent focal power is provided by the diffractive waveplate coatings with lensing properties 420 and 460 in FIG. 4A and FIG. 4B.

In alternative embodiments, both the diffractive waveplate coating with lensing properties 420 and the polarization conversion coating 425 in FIG. 4A and FIG. 4B can be replaced by a lens fabricated from a birefringent crystal, or a birefringent liquid crystal layer with curved bounding surfaces. Similarly, both the diffractive waveplate coating with lensing properties 460 and the polarization conversion coating 450 in FIG. 4A and FIG. 4B could be replaced by a lens fabricated from a birefringent crystal, or a birefringent liquid crystal layer with curved bounding surfaces.

Although the invention disclosed here provides an energized lens system that can be used for many different purposes, favorable applications are to ophthalmic lens devices including spectacles, contact lenses, and intraocular lenses. These are favorable applications because the reduction in size (especially thickness), weight, and power consumption allowed by reducing the number of switched optical layers from two to one will be highly beneficial in these particular applications.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A polarizer-free single chamber energized lens system comprising:
    a front optical system having at least a static refractive layer with a curved front surface and a curved back surface, and a focal length that is different for two polarizations of light;

a twisted nematic liquid crystal layer having at least a front curved surface, a back curved surface, and a nematic liquid crystal between the front curved surface and the back curved surface;

the front curved surface having at least a transparent conductive electrode and an alignment layer for aligning a portion of the liquid crystal adjacent to the alignment layer;

the back curved surface having at least a transparent conductive electrode and an alignment layer for aligning a portion of the liquid crystal adjacent to the alignment layer of the back curved surface, the alignment layer of the back curved surface oriented perpendicular to the alignment layer of the front curved surface; the front curved surface and the back curved surface having different radii of curvature;

a thickness of a liquid crystal layer passing light therethrough meeting a Mauguin condition;

a back optical system having at least a static refractive layer with a curved front surface and a curved back surface, and a focal length that is different for two polarizations of light; and a controller located outside an optical zone that enables application of an electric field between the transparent conductive electrodes of the twisted nematic liquid crystal layer, wherein the energized lens system is configured such that a focal length is different when an electric field is applied between the transparent conductive electrodes than when no such electric field is applied, and the focal length of the energized lens system is independent of the polarization of light whether or not an electric field is applied between the transparent conductive electrodes, wherein a single focal length is achieved with a single switchable liquid crystal layer, without a polarizer.

2. The energized lens system of claim 1 wherein the front optical system comprises a diffractive waveplate coating having lensing properties and a coating for conversion of circularly polarized light to linearly polarized light, and the back optical system comprises a coating for conversion of linearly polarized light to circularly polarized light and another diffractive waveplate coating having lensing properties.

3. The energized lens system of claim 1, wherein the energized lens system is configured as an ophthalmic lens device.

4. The energized lens system of claim 2, wherein the energized lens system is configured as an ophthalmic lens device.

5. The energized lens system of claim 1, wherein the energized lens system is configured as a contact lens.

6. The energized lens system of claim 2, wherein the energized lens system is configured as a contact lens.

7. The energized lens system of claim 1, wherein the energized lens system is configured as an intraocular lens.

8. The energized lens system of claim 2, wherein the energized lens system is configured as an intraocular lens.

9. The energized lens system of claim 1, wherein the energized lens system is configured as a spectacle lens.

10. The energized lens system of claim 2, wherein the energized lens system is configured as a spectacle lens.

11. The energized lens system of claim 1, wherein the Mauguin condition, includes:

$$d >> \lambda/2\Delta n \text{ where, } \lambda$$

is a wavelength of the light transmitted through the layer, $\Delta n$ is birefringence of the liquid crystal filling the space between two boundary surfaces of the layer, and radii of curvature of the two boundary surfaces are different so that a layer produces a focusing or defocusing effect, and thickness d of the layer varies with transverse position.

12. The energized lens system of claim 1, wherein the Mauguin condition is met at all transverse positions of the layer through which light is transmitted, and at all wavelengths within an operating wavelength band of the layer.

13. The energized lens system of claim 1 wherein the front optical system comprises a birefringent crystal with curved bounding surfaces, and the back optical system comprises a birefringent crystal with curved bounding surfaces.

* * * * *